United States Patent [19]
Soled et al.

[11] Patent Number: 5,157,199
[45] Date of Patent: Oct. 20, 1992

[54] ISOMERIZATION OF PARAFFINS WITH STRONG SOLID ACID CATALYST AND ADAMANTANE

[75] Inventors: Stuart L. Soled, Pittstown; Enrique Iglesia, Clinton; George M. Kramer, Berkeley Heights; William E. Gates, Somerset; Richard H. Ernst, Glen Gardner, all of N.J.

[73] Assignee: Exxon Research and Engineering Co., Florham Park, N.J.

[21] Appl. No.: 677,905

[22] Filed: Apr. 1, 1991

[51] Int. Cl.⁵ .............................................. C07C 5/13
[52] U.S. Cl. ..................................... 585/750; 585/734
[58] Field of Search .............................. 585/750, 734

[56] References Cited

U.S. PATENT DOCUMENTS 4,357,484  11/1982  Kramer .................................. 585/740

OTHER PUBLICATIONS

M. Y. Wen: "Hydroconversion of heavier n-paraffins with Platinum: Zirconia: Sulfate(2-)" ACS Symp. Series 35, 819-20 (1990): CA Abstract CA 1;4: 9302e.

*Primary Examiner*—Asok Pal
*Assistant Examiner*—P. Achutanurthy
*Attorney, Agent, or Firm*—Jay Simon

[57] ABSTRACT

A process for isomerizing a paraffin feed comprising contacting the feed with a strong, solid acid catalyst comprising a sulfated Group IVB metal oxide and at least one Group VIII metal in the presence of hydrogen and an adamantane compound.

14 Claims, 3 Drawing Sheets

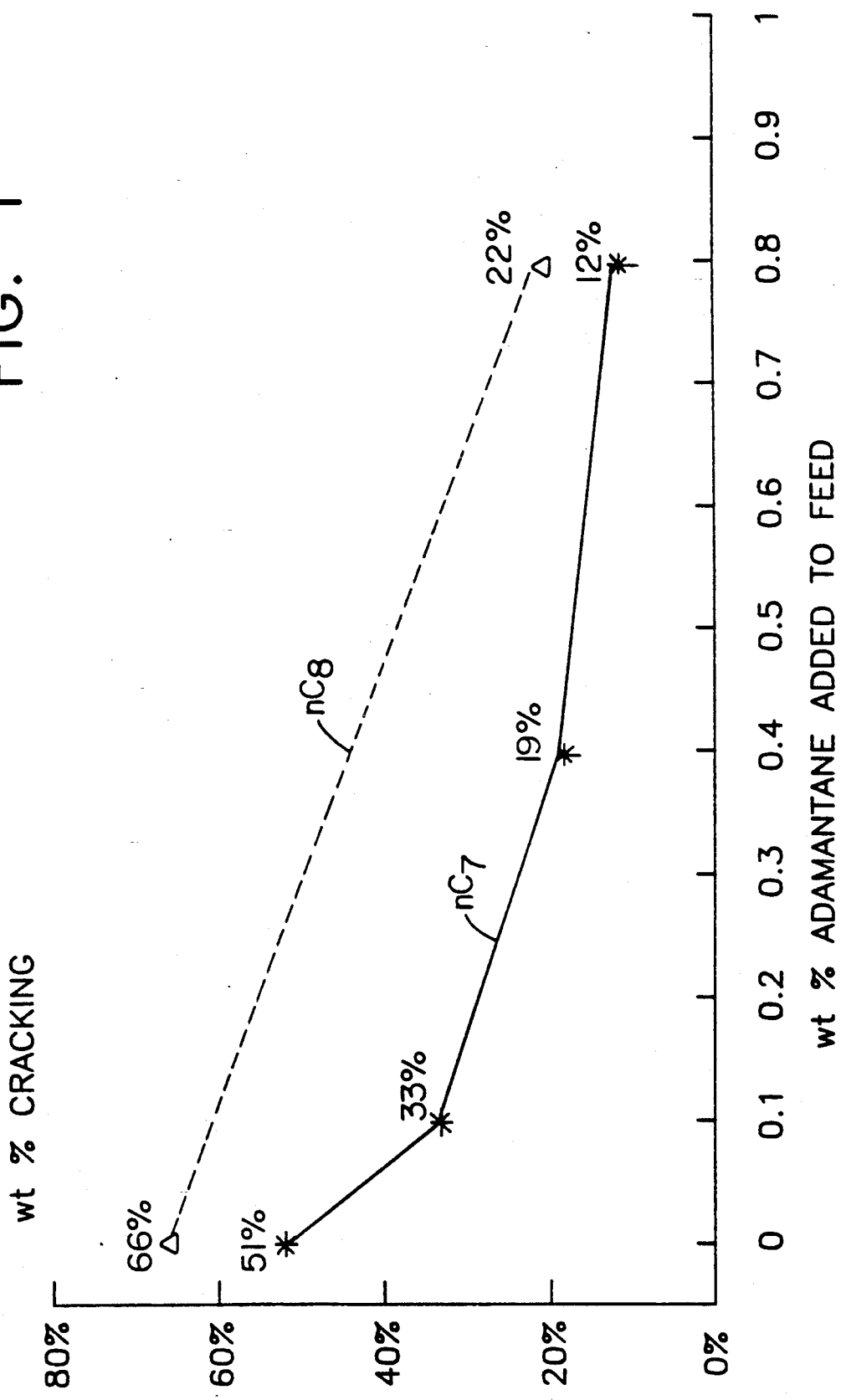

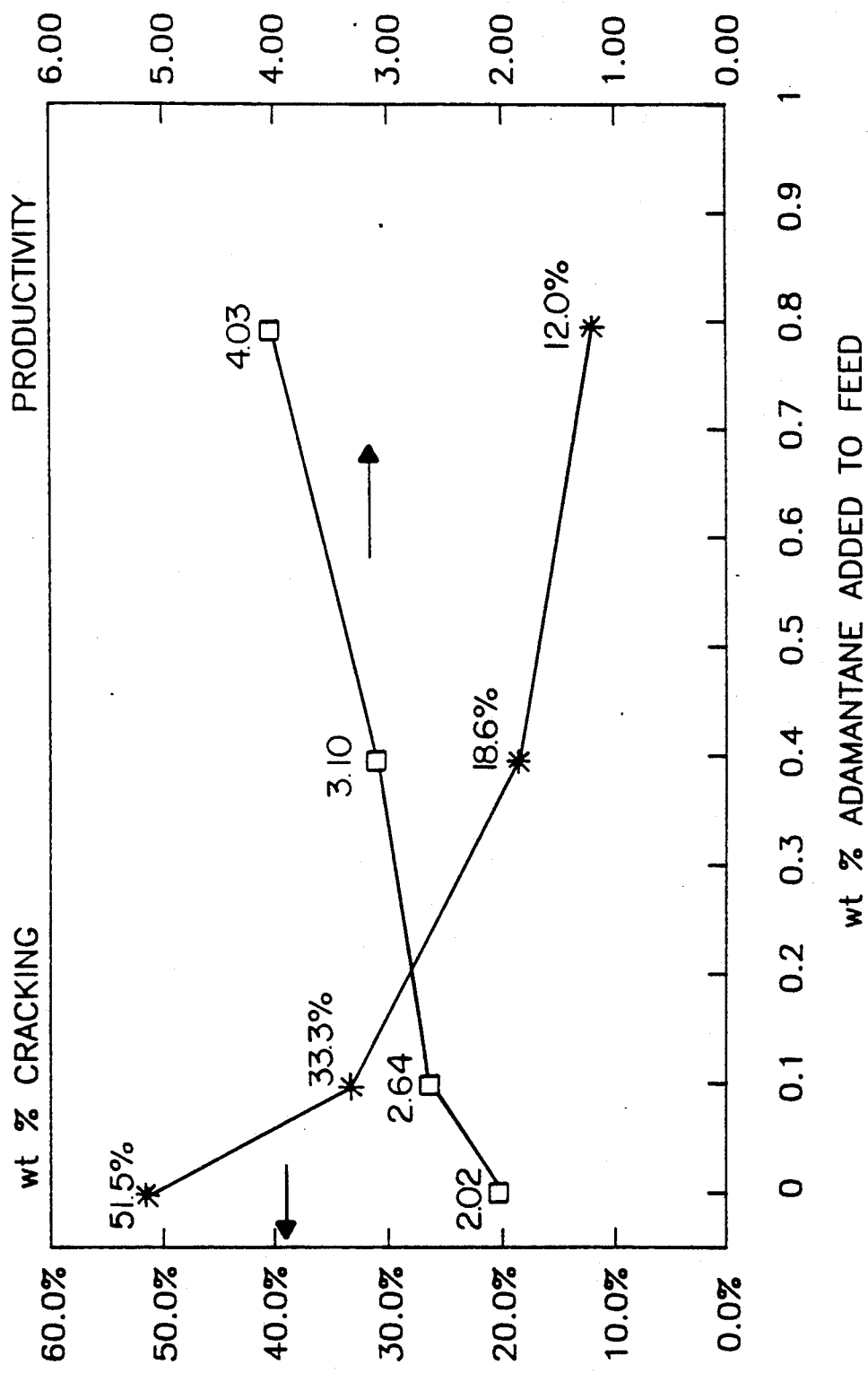

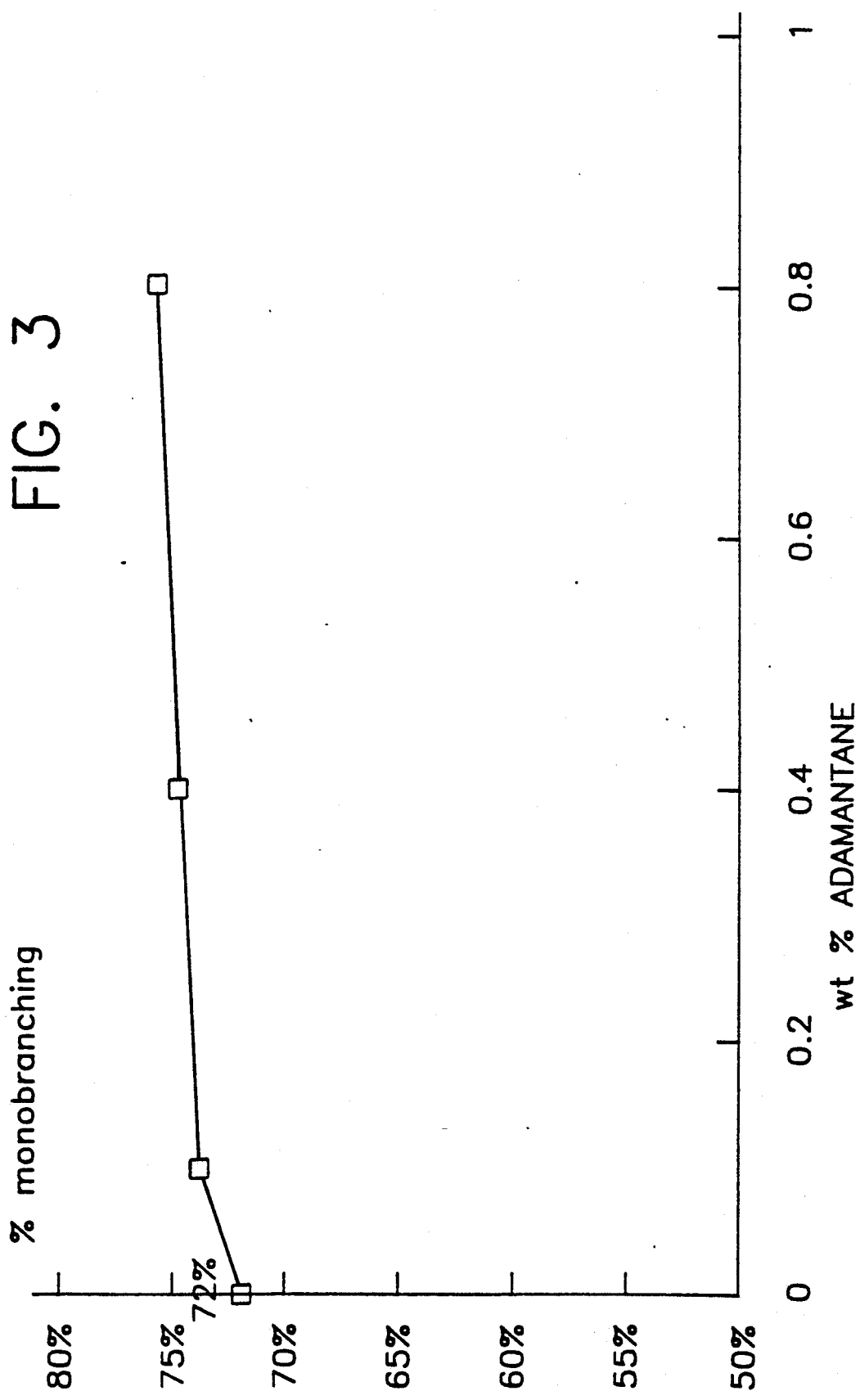

ISOMERIZATION OF PARAFFINS WITH STRONG SOLID ACID CATALYST AND ADAMANTANE

BACKGROUND OF THE INVENTION

1. Field of the Invention

The invention is a process for isomerizing paraffinic hydrocarbons with a strong acid, solid catalyst comprised of a sulfated Group IVB metal and at least one Group VIII metal in the presence of hydrogen and an adamantane or adamantane derivative.

2. Background Information

Several catalytic methods have been used for isomerizing hydrocarbons. Many have required high temperatures, expensive or hard to handle catalysts, expensive corrosion-resistant equipment, or complex recovery procedures for carrying out extensive isomerization. The commercial catalysts used in isomerizing hydrocarbons include aluminum halides, hydrogen fluoride, sulfuric acid and the like. However, the selective isomerization of long chain paraffins is not practiced with these catalysts because it is difficult to control side reactions. Aside from this, it has long been recognized that sulfuric acid and halide-containing catalysts may cause environmental problems, since in many instances they are highly corrosive and not easily disposable. What is ultimately desired is a catalyst that can achieve both high selectivity and a high degree of branching from long chain normal paraffins (those containing 7 or more carbon atoms) under mild conditions thereby avoiding substantial side reactions, such as cracking. The ideal catalyst would be capable of catalyzing the isomerization reaction at low temperatures by providing strong acid sites for catalysis. Sulfate ion modified zirconia has been found to be a very reactive solid superacid, see Hino, M. et al., *Chem. Lett.*, pp. 1671-1672 (1981). U.S. Pat. No. 3,032,599 describes a process for isomerizing $C_5$- normal paraffins using sulfate ions to enhance the acidity of zirconia catalysts containing platinum. European Patent 0174836 describes a similar catalytic method for isomerizing $C_6$- normal paraffins.

It has been found that platinum in the presence of hydrogen prevents the solid superacid catalyst from deactivating. While not wishing to be bound by theory, it is believed that Pt hydrogenates the olefinic components produced from carbonium ion intermediates developed in the isomerization reaction. These intermediates are believed to be the precursors for the deactivating residues. T. Hsoi et al., *ACS Preprints Symp. Ser.* 33(4), pp. 562-567 (1988) describes isomerizing normal $C_5$-$C_6$ paraffins with a so super acid catalyst. Hsoi uses sulfated transition metal oxides, such as sulfated zirconia, which exhibits superacidity and shows catalytic activity even at low reaction temperatures. The acid strengths of the solid superacids were measured by the color change of a Hammett indicator. The Ho acid strengths were found to be greater than or equal to $-14.5$ and less than or equal to $-16.4$. Only a small amount of Pt is necessary to improve catalyst activity, catalyst life, and avoid coke deposits. For example, a metal loading of only 0.50 wt. % Pt to a sulfated $ZrO_2$ catalyst improved catalyst activity remarkably and the catalyst maintained its initial activity after 100 hours of use at conversion temperatures of at least 140° C. The results suggest that a Pt/sulfated $ZrO_2$ catalyst exhibits the superacidity and high activity necessary to make commercial low temperature catalyzed isomerization reactions possible.

M. W. Wen et al., *Energy & Fuels*, Vol. 4, pp. 372-379 (1990), studied the formation of highly branched long chain paraffins and highly isomerized short chain paraffins produced from a normal hexadecane feed. The isomerization selectivity observed by Wen was 90 percent in making short chain isoparaffins. The conclusion reached in this study was that Pt/sulfated $ZrO_2$ catalysts are more effective for hydrocracking heavier normal paraffins, i.e. normal paraffins having four or more carbon atoms, than for hydroisomerizing short chain normal paraffins, based on the relatively low selectivity and the amount of short chain isoparaffins produced (see page 373).

M. Y. Wen et al., *A.C.S. Symposium Series*, Vol. 35, No. 4, pp. 819-820 (1990), adds methylcyclopentane to a Pt/sulfated $ZrO_2$ catalyst to improve isomerization activity.

Despite the advances made in solid, superacid isomerization, the catalysts found in the prior art continue to suffer major disadvantages when applied, for example, to long chain hydrocarbons e.g., $C_7+$. For instance, large amounts of byproducts, consisting predominantly of cracked hydrocarbon materials, form in prior art isomerization methods along with the desired isomerate product. Cracking reduces the amount of long chain paraffins available for isomerization, thereby reducing the ultimate yield.

In U.S. Pat. No. 4,357,484, Kramer discloses an isomerization process where adamantane is added to halide-containing Lewis Acid catalysts. A detailed look at the isomerization mechanism in Kramer reveals that the catalyst must generate carbonium ion intermediates in solution to effect the isomerization. Therefore, halide-containing Lewis Acid catalysts, such as aluminum bromide, are added to a solvent.

U.S. Pat. No. 3,671,598 describes a commercial process for isomerizing cyclic hydrocarbons with liquid acids such as sulfuric or fluorosulfonic acid in the presence of adamantane.

Under conditions where the isomerization reaction proceeds at rates useful for commercial applications, long chain paraffins (i.e., $C_7+$ paraffins) crack extensively. Both cracking and isomerization occur at the acid sites of the catalyst. Partially poisoning the catalyst, for example, adding small amounts of aromatics, reduces the amount of undesirable cracked products that form at the expense of reduced productivity.

The term "productivity", used herein, is defined as the weight of paraffinic branched hydrocarbon isomerate produced by the catalyst per weight of catalyst per unit time e.g., g iso $C_n$/g cat/hr, where $n=6$ or more, at a particular reaction temperature which ranges from 0° C. to 400° C. Productivity is obtained by multiplying product yield, having the units weight product/weight feed, by the weight hourly space velocity, having the units weight feed/weight catalyst/hour.

An object of the present invention is to provide an economical method for isomerizing long chain paraffins, easily controllable that enables the isomerization to occur productively at low temperatures, and does not involve complex or difficult separation and recovery procedures.

Another object of the invention is to provide an isomerization method where the catalyst can be regenerated readily.

Yet, another object of the invention is to provide a fixed-bed isomerization process that uses a strong acid, solid catalyst with no need for any solvent or liquid phases at reaction conditions, other than the feed. At reaction temperatures the lower boiling feeds will normally be in the vapor phase, but some liquid feed may be present with higher boiling paraffins.

SUMMARY OF THE INVENTION

We have discovered that when a $C_7+$ paraffin feed is isomerized in the presence of hydrogen, an adamantane, and a strong acid, solid catalyst, such as a Group VIII metal supported on a sulfated Group IVB oxide the amount of undesirable cracked hydrocarbon products is drastically reduced and the productivity is increased. The adamantane compound increases productivity and the isomerization rate. Simultaneously, the amount of undesirable cracked hydrocarbons such as propane, butane, isobutane and isopentane, typically obtained in isomerization reactions, are greatly reduced, while the degree of branching in the isomerate product is substantially unaffected.

The reaction is preferably carried out in the absence or substantial absence of any liquid phase other than feed. Liquid phase or slurry phase catalysts are also absent to the extent they would contribute to the isomerization process. In a preferred embodiment, the process involves only a gaseous feed and a solid catalyst with no liquid phase of any kind.

The feeds are usually normal paraffins, preferably $C_5$ or $C_5+$, more preferably $C_7$ or $C_7+$, still more preferred $C_7-C_{30}$, and most preferred $C_7-C_{20}$. The isomerate of a $nC_n$ molecule is an iso $C_n$ molecule, while the crackate will be a $C_{(n-1)}-$ molecule, of which propane and isobutane are the primary components. By virtue of this invention the crackate selectivity is less than about 20 wt. %, preferably less than about 15 wt. %, based on weight of product.

The reaction rate of this process is also much faster than an isomerization process without an adamantane. Thus, the process can result in higher daily throughputs (important for commercial processes) and less time at temperature for the feed, further reducing cracking tendencies. The reaction rate is at least about 1.5 times that of a process without the adamantane compound, preferably at least about 2.0 times that rate.

BRIEF DESCRIPTION OF THE DRAWINGS

FIG. 1 shows that the wt. % cracking (cr/cr+isom) steadily decreases for n-heptane and n-octane feeds catalyzed by $Pt/ZrO_2/SO_4$ when adamantane is added to the feed.

FIG. 2 shows an increase in catalyst productivity (g $C_7$ isom./g.cat/hr) and a decrease in the cracking selectivity for n-heptane feed catalyzed with a $Pt/ZrO_2/SO_4$ isomerization catalyst when adamantane is added to the feed.

FIG. 3 shows that adding adamantane to an $nC_7$ feed does not substantially change the % monobranching of the isomerate product.

DETAILED DESCRIPTION

The invention is a process for isomerizing paraffins of seven or more carbon atoms (i.e. $C_7+$ paraffins) into branched long chain hydrocarbons under conditions sufficient to reduce the amount of cracked hydrocarbon products formed, comprising contacting the $C_7+$ paraffin feed with a strong acid, solid catalyst comprising a sulfated Group IVB metal oxide and at least one Group VIII metal, in the presence of hydrogen and adamantane and in the absence of a liquid catalyst phase, e.g., an acid or halide-containing catalyst in either liquid or slurry. In the present invention a Group IVB metal oxide, preferably zirconia, is incorporated with a sulfate or a sulfate precursor. Sources of Group IVB metal oxides include Group IVB metal salts and alkoxides. For example, if zirconia is used in the present invention then the source of zirconia includes zirconium salt solutions, such as, zirconium oxychloride or zirconyl nitrate that are soluble in water and can be precipitated as a hydroxide upon adding a base. The zirconia source is dissolved in water, a base, e.g., $NH_4OH$ is added to adjust the pH of the solution in the range of from about 9 to about 11 to form a zirconium hydroxide precipitate. Another source of zirconia is zirconium alkoxide such as, zirconium n-propoxide, which may be hydrolyzed to form zirconium hydroxide. The zirconium hydroxide may then be incorporated with the sulfate and Group VIII metal. The Group VIII and Group IVB metals suitable for use in the present invention are described in Weast, *Handbook of Chemistry and Physics*, 57th Edition, 1976-77.

Alternatively, the zirconium hydroxide may be calcined at temperatures ranging from 450° C. to 650° C. in order to convert the zirconium hydroxide to zirconium oxide, which also can be incorporated with the sulfate and Group VIII metal.

The order of incorporating the zirconium hydroxide or oxide with the sulfate or the Group VIII metal is not critical. The preferred catalyst preparation method involves incorporating the sulfate with, for example, zirconium hydroxide then adding the Group VIII metal.

Any material capable of forming a sulfate when calcined may be used to provide the sulfate. Preferably, this includes hydrogen sulfide, sulfur dioxide, mercaptans and sulfur- and halo-containing compounds such as fluorosulfonic acid, sulfuryl chloride or thionyl chloride, and mixtures thereof.

The sulfate can be incorporated with the zirconium by one of several techniques known in the art. For example, a zirconium hydroxide or zirconium oxide, can be immersed in an aqueous solution containing sulfuric acid ($H_2SO_4$) then dried at 110° C. Alternatively, the sulfate can be incorporated with the zirconium component by impregnating a zirconium hydroxide or zirconium oxide with a sulfate solution which preferably is an ammonium sulfate solution and dried at about 100° to 150° C., e.g., 110° C.

The Group VIII metal may be incorporated by a number of methods with the zirconium hydroxide or oxide to which sulfate has been added as previously described. For example, a sulfated zirconium hydroxide or oxide can be immersed in a solution containing a water soluble Group VIII metal salt. In a preferred embodiment, the sulfated zirconium hydroxide or oxide is immersed in an aqueous solution of chloroplatinic acid or tetra-amine-platinum hydroxide and dried. Also, the sulfated zirconium hydroxide or oxide can be impregnated with an aqueous solution of a water soluble Group VIII metal salt or acid, e.g., chloroplatinic acid or salts thereof and dried.

The Group VIII metal is preferably selected from the Group consisting of nickel, platinum, ruthenium, rhodium, palladium, osmium, and iridium. Sulfated Group VIII metals may also be used and may be selected, for example, from nickel sulfate, platinum sulfate, palladium sulfate, ruthenium sulfate and nickel ammonium sulfate. The Group-VIII metal sulfates can be incorporated with zirconium hydroxide or zirconium oxide by impregnation using an aqueous solution of, for example, nickel sulfate.

The relative amount of Group VIII metal to be incorporated with the Group IVB metal oxide, preferably ranges from about 0.01 to about 10 parts by weight of Group VIII metal per 100 parts by weight of Group IVB metal oxide. The sulfate concentration when, for example, a sulfuric acid solution is used, is preferably 0.01 N to 10N, and more preferably 1N to 5N.

After the sulfate and Group VIII metal have been incorporated with the zirconium hydroxide or and calcined in air or in an oxidizing atmosphere, e.g., a 1% $O_2$, 99% $N_2$ stream. The calcination is carried out at temperatures of 450° C. to 650° C. and more preferably at 500° C. to 600° C. for a time sufficient to convert the hydroxide to the oxide and bind the surface sulfate phase to the oxide, e.g., about 0.5 hours to about 30 hours, and preferably for about 1 hour to about 24 hours. In the most preferred embodiment the calcination is carried out at 550° C.-600° C. for about 0.5 hour to about 10 hours.

The sulfate concentration remaining on the catalyst, after the calcination step, preferably ranges from about 3.0 wt. % to about 5.0 wt. %, based on the weight of Group IVB metal oxide.

Catalysts prepared in the above manner exhibit excellent catalytic activity for $C_7+$ paraffin isomerization.

Before the catalyst is used in an isomerization reaction, it is preferably reduced in hydrogen or a hydrogen containing stream at temperatures ranging from about 100° C. to about 400° C. and more preferably from about 100° C. to about 200° C. Reducing the Group VIII metal stabilizes catalyst activity. However, reduction temperatures above about 400° C. decompose the sulfate. Subjecting the catalyst to reducing conditions provides the catalyst with hydrogenation functionality for hydrogenating fractions and polymerizable olefins formed during the process. Temperatures up to about 200° C. are usually adequate to reduce the Group VIII noble metals to the elemental state. Higher temperatures are not necessarily required for the non-noble Group VIII metals, e.g., NiO, is a hydrogenation catalyst.

The adamantane may be added to the process at any time, preferably prior to the feed being contacted with the catalyst; more preferably, the adamantane is dissolved in the feed. Adamantane compounds suitable for use in the present invention contain at least one unsubstituted bridgehead position and are prepared by conventional methods, such as those described in U.S. Pat. Nos. 3,382,288 and 3,546,308. The adamantyl ring structure of the adamantane may either be unsubstituted or substituted with linear or branched $C_1$-$C_4$ units, such as alkyl, and more specifically, methyl, ethyl, n-propyl, isopropyl, n-butyl, isobutyl, t-butyl units and the like. Substituted adamantane include 1-methyladamantane, 2-methyladamantane, 1,3-dimethyl-adamantane, and the like. However, unsubstituted adamantane is most preferred. The adamantyl compound is used in sufficient amount to reduce excessive cracking. Preferably, the amount of adamantane added to the process preferably ranges from about 0.01 wt. % to about 5.0 wt. % based on the total weight of the feed.

According to the present invention the isomerization reaction is conducted in the absence of a solvent or liquid acid catalyst and is free of halide-containing compounds, such as that used in previously mentioned U.S. Pat. No. 4,357,484.

The isomerization reaction is carried out at temperatures at or below about 400° C. At reaction temperatures greater than 400° C., particularly in the presence of hydrogen, the sulfate component has a tendency to decompose thereby lowering the acid strength of the catalyst and preventing the isomerization reaction from proceeding. Preferably, the reaction is carried out at temperatures between about 70° C. to about 250° C. The reaction pressure ranges from about 100 kPa to about 3000 kPa and more preferably ranges from about 100 kPa to about 500 kPa. The weight hourly space velocity (WHSV) ranges from 1 (wt feed/wt catalyst/hr) to 20 (wt feed/wt catalyst/hr). The mole ratio of hydrogen to paraffin feed ranges from about 0.1 to about 10.

The catalyst of the present invention is highly active at lower temperatures and particularly useful for the isomerization of light petroleum fractions to obtain higher octane number products. The thermodynamic equilibrium of short chain low molecular weight paraffinic hydrocarbons in the low temperature regions, below about 400° C., favors more higher octane number, highly branched paraffins, than in the high temperature regions, e.g., above about 400° C.

Previously, it was believed that rapid alkane isomerizations that occur by the propagation of a carbonium ion chain reaction were best conducted in halide-containing acid catalyst systems, such as those containing $AlBr_3$, $AlCl_3$ and the like. We have unexpectedly found that selective catalytic alkane isomerizations that proceed by carbonium ion chain reactions also occur in non-halided strong acid, acid catalyst systems where they are catalyzed by the presence of adamantane.

Apparatus useful for carrying out the present isomerization method may be selected from conventional laboratory, pilot plant, or full industrial scale equipment. The method may be carried out batch or continuous preferably a continuous, fixed bed operation.

The sulfated Group IVB metal catalyst can be regenerated by a calcination procedure as previously described, followed by reduction, also in the manner previously described.

EXAMPLE 1

Preparation of Platinum Solution

Chloroplatinic acid (6.25 g), containing 40.0 wt. % Pt, was placed in a one liter volumetric flask. Water was added to the flask dissolving the chloroplatinic acid and bring the total volume in the flask to one liter, such that 20 cc of the solution contained 0.05 g Pt.

EXAMPLE 2

Preparation of $Zr(OH)_4$ $ZrOCl_2.H_2O$ (360 g) was dissolved in water (2800 cc). A concentrated ammonium hydroxide solution (14M) was then added as the entire solution was stirred until the pH of the solution (now a slurry mixture) reached 10 as a precipitate formed. The mixture was allowed to sit for two hours, and the precipitate was filtered and washed twice with distilled water and twice with water containing enough ammonium hydroxide to bring the pH of the water to 10. The solid precipitate was reslurried into a 1M solution of ammonium hydroxide, heated to 60° C., and stirred. After one hour, the solution was filtered and washed with water to remove any residual chloride. The resulting zirconium hydroxide (Zr(OH)$_4$) powder obtained was dried overnight at 110° C.

EXAMPLE 3

Preparation of Pt/ZrO$_2$/SO$_4$

The dried Zr(OH)$_4$ powder (10 g) prepared in Example 2 was placed in 20 cc of the chloroplatinic acid (platinum) solution prepared in Example 1 to form a slurry. The slurry was stirred for 5 minutes, filtered and dried overnight at 110° C. The dried solid was then placed in 22 cc of 1N sulfuric acid, stirred for 5 minutes, filtered and again dried overnight at 110° C. The resulting Pt/ZrO$_2$/SO$_4$ catalyst was then calcined at 600° C. for 3 hours in air.

EXAMPLE 4

Catalytic Reaction

The catalyst formed in Example 3 was pelleted and screened to 40/60 mesh. Immediately prior to loading, the catalyst was recalcined in air at 600° C. for 1 hour to remove any water that may have readsorbed onto the catalyst's surface. The catalyst, together with a quartz powder diluent, was added to a six inch reactor bed. A thermocouple was inserted into the center of the bed. Hydrogen (500 cc/min) was passed over the bed at 200° C. for 60 minutes. A n-heptane or n-octane feed was introduced via a liquid feed pump, such that 10 to 20 grams of feed passed over the bed per gram of catalyst per hour. Adamantane was dissolved in the n-heptane or n-octane feed in amounts ranging from about 0.1 to about 0.8 weight percent based on the total weight of the feed. Hydrogen was simultaneously passed through the bed such that the ratio of hydrogen (cc/min) to feed (gm/hr) was approximately 17, corresponding to a molar hydrogen:feed ratio of about 4.5. The products were analyzed on a gas chromatograph equipped with a capillary column. The results are shown in FIGS. 1, 2 and 3, discussed below.

FIG. 1 shows that in the absence of adamantane (0 wt. %) substantial cracking occurs and that when adamantane is added a significant reduction in cracking of the n-heptane and n-octane feed occurs. Cracking is a significantly competitive reaction to isomerization for normal C$_7$ and C$_8$ feeds. For normal C$_7$, the weight percent of cracked products resulting from the isomerization at 200° C., 15.5 WHSV and 790 kPa (at approximately 25% conversion) over Pt/ZrO$_2$/SO$_4$ without adamantan is slightly more than 50 wt. %. The predominant cracked hydrocarbon products were isobutane and propane. However, adding adamantane reduced the amount of cracked products remarkably. For instance, adding 0.8 wt. % adamantane reduced the level of cracking from 50 wt. % to only 12 wt. %. The weight percent of cracked products for the normal C$_8$ feed was also reduced from 66 wt. % (no adamantane) to 22 wt. % by adding 0.8 wt. % adamantane. In systems without adamantane at least about 50% of the recovered carbon is found in the crackate; in systems with adamantane only about 20 wt. % or less of the carbon recovered is in the crackate.

FIG. 2 shows that besides reducing the cracking that occurs during normal C$_7$ isomerization (at 200° C., 15.5 WHSV, 100 psi), productivity is increased by a factor of two (2) when 0.8 wt. % adamantane is added to the feed. As the amount of adamantane is steadily increased up to 0.8 wt. %, under a constant set of reaction conditions, both the conversion increases as the amount of adamantane increases and the selectivity ratio of isomerization products to cracking products increases As a result, the yield of C$_7$ isomerate and the productivity are doubled upon the addition of 0.8% adamantane. This behavior differs from that of adding aromatics, which under some conditions, are known to enhance isomerization selectivity, but lower the overall isomerization rate and the productivity.

FIG. 3 shows that branching of the C$_7$ isomerate product (200° C., 100 psi, 15.5 WHSV, 0-0.8 wt. % adamantane) changes slightly when adamantane is added and that the amount of monobranched isomers increases slightly.

What is claimed is:

1. An isomerization process which comprises contacting a feed comprising normal C$_n$ or C$_{n+}$ paraffins, where n=5, with a solid catalyst comprising a Group VIII metal and a sulfated Group IVB oxide, in the presence of hydrogen and an adamantane compound, at temperatures below the sulfate decomposition temperature and recovering a product comprising iso C$_n$ or iso C$_{n+}$ isomerate and C$_{(n-1)}-$ crackate.

2. The process of claim 1 wherein the reaction temperature is below about 400° C.

3. The process of claim 1 wherein the feed comprises C$_{7+}$.

4. The process of claim 1 wherein the Group VIII metal is a noble metal.

5. The process of claim 4 wherein the noble metal is platinum.

6. The process of claim 1 wherein the Group IVB metal oxide is zirconia.

7. The process of claim 1 wherein the adamantane compound is present in an amount of about 0.01 to 5.0 wt. % based o weight of feed.

8. The process of claim 1 wherein the mole ratio of hydrogen:feed is above about 1:1.

9. The process of claim 8 wherein the ratio is about 1:1 to about 10:1.

10. An isomerization process which comprises contacting a C$_{7+}$ paraffin feed with a catalyst comprising platinum and a sulfated zirconia in the presence of hydrogen and an adamantane compound at temperatures below about 400° C., and recovering a product having less than about 20 wt. % crackate.

11. The process of claim 10 wherein the feed comprises C$_7$-C$_{30}$ paraffins.

12. The process of claim 11 wherein the ratio of adamantane compound to feed is about 0.01 to 5.0 wt. %.

13. The process of claim 12 wherein the feed is gaseous and there is substantial absence of any liquid phase.

14. The process of claim 1 conducted in the substantial absence of a liquid phase.

* * * * *